United States Patent
Neare-Vaarmann

(10) Patent No.: US 9,302,403 B2
(45) Date of Patent: Apr. 5, 2016

(54) FOOD CUTTING APPARATUS

(75) Inventor: Önne Neare-Vaarmann, Luige alevik (EE)

(73) Assignee: Smartest Invest Ou, Luige Alevik (EE)

( * ) Notice: Subject to any disclaimer, the term of this patent is extended or adjusted under 35 U.S.C. 154(b) by 258 days.

(21) Appl. No.: 14/114,018

(22) PCT Filed: Mar. 27, 2012

(86) PCT No.: PCT/EP2012/055360
§ 371 (c)(1),
(2), (4) Date: Oct. 25, 2013

(87) PCT Pub. No.: WO2012/146449
PCT Pub. Date: Nov. 1, 2012

(65) Prior Publication Data
US 2014/0047965 A1   Feb. 20, 2014

(30) Foreign Application Priority Data
Apr. 27, 2011   (EE) ................ 201100037 U

(51) Int. Cl.
| | |
|---|---|
| *B26D 3/18* | (2006.01) |
| *B26D 5/10* | (2006.01) |
| *B26D 7/06* | (2006.01) |
| *B26D 7/18* | (2006.01) |
| *C12Q 1/68* | (2006.01) |
| *B26D 5/22* | (2006.01) |
| *B26D 5/18* | (2006.01) |

(52) U.S. Cl.
CPC ............... *B26D 3/185* (2013.01); *B26D 5/10* (2013.01); *B26D 5/22* (2013.01); *B26D 7/0608* (2013.01); *B26D 7/1818* (2013.01); *C12Q 1/6886* (2013.01); *B26D 3/18* (2013.01); *B26D 5/18* (2013.01); *C12Q 2600/158* (2013.01); *C12Q 2600/178* (2013.01); *Y10T 83/6481* (2015.04)

(58) Field of Classification Search
CPC ............ B26D 3/18; B26D 3/185; B26D 5/10; B26D 5/18; B26D 5/22; B26D 7/0608; B26D 7/1818; Y10S 83/932; Y10T 83/6481
See application file for complete search history.

(56) References Cited

U.S. PATENT DOCUMENTS

| | | | |
|---|---|---|---|
| 2,303,595 A | 12/1942 | Young | |
| 2,341,582 A | 2/1944 | Turner | |
| 2,353,607 A | 7/1944 | Young | |
| 7,587,968 B1 * | 9/2009 | Roberts | B26D 3/185 83/404.3 |

FOREIGN PATENT DOCUMENTS

| | | | |
|---|---|---|---|
| FR | 2745219 A1 * | 8/1997 | |
| GB | 471 678 A | 9/1937 | |
| GB | 2 246 510 A | 2/1992 | |

* cited by examiner

*Primary Examiner* — Stephen Choi
(74) *Attorney, Agent, or Firm* — Ladas & Parry LLP

(57) ABSTRACT

The present invention relates to a device for cutting material, mainly foods, vegetables or fruits. The device comprises housing with a cutting chamber having open top, inside the cutting chamber there is a movable first cutter and at the bottom of the chamber a stationary second cutter. Device comprises a lever attached pivotally to the housing, wherein the lever is attached in an articulated manner to a first cutter such that when lever is pivoted, the first cutter is moved along the bottom of the chamber from one end of the chamber towards the first material ejector. The further movement of the lever moves the first cutter into the first material ejector for ejecting material from between the cutting edges of the first cutter and moves the second ejector also attached to the lever into the cutting chamber for ejecting material through the cutting edges of the second cutter.

4 Claims, 4 Drawing Sheets

FOOD CUTTING APPARATUS

RELATED APPLICATION INFORMATION

This application is a 371 of International Application PCT/EP2012/055360 filed 27 Mar. 2012 entitled "Food Cutting Apparatus", which was published in the English language on 1 Nov. 2012, with International Publication Number WO 2012/146449 A1, and which claims priority from Estonia Patent Application U201100037 filed 27 Apr. 2011, the content of which is incorporated herein by reference.

TECHNICAL FIELD

The present invention relates to a device for cutting material, preferably for chopping material into rectangular or cubical pieces. More particularly the present invention relates to a hand operated device for chopping material, mainly foods, vegetables or fruits, into cubes.

In the following specification the term "material" indicates solid foods (treated on untreated), vegetables or fruits to be cut.

BACKGROUND ART

The prior art includes many known devices for cutting material into slices or rectangular pieces.

U.S. Pat. No. 2,341,582 (published 15 Feb. 1944) describes a device for cutting foods. This device includes a cutting chamber with open top, where at the one end of the chamber there is a stationary cutter with cutting edges and at the other end of the chamber there is a material ejector, which is movable by the shaft operated by the crank handle from the end of the chamber towards the cutter. Moving ejector pushes the material to be cut through the cutting edges of the cutter, as a result slices of the material emerge between the cutting edges. At the end of the shaft a rotating blade is attached, which cuts the material slices emerging from between the cutting edges into smaller pieces (cubes).

From the United Kingdom patent application GB2246510A (published 5 Feb. 1992) a device for cutting foods is known. This device comprises a cutting chamber, where two traverse walls of the chamber include first and second cutters correspondingly. The material to be cut is placed in front of the first cutter and the material is pushed with the ejector attached to the pivotable lever through the first cutter into the cutting chamber. Thereafter lever is pivoted in the opposite direction and said lever pushes second material ejector into the cutting chamber, which pushes the material, which was cut by the first cutter, through the second cutter and out of the cutting chamber.

From the U.S. Pat. No. 2,353,607 (published Jul. 11, 1944) is known a device for cutting foods, comprising in the housing a cutting chamber and two stationary cutters, where first cutter is placed correspondingly in the side wall of the cutting chamber and the second cutter in the bottom of the cutting chamber.

Material to be cut is placed in front of the first cutter in the side wall of the cutting chamber outside of the chamber. By pivoting a lever the material is pushed through the first cutter into the cutting chamber by the first material ejector, which is attached in an articulated manner to the lever. Then by pivoting the lever in another direction, the second material ejector, moving along grooves in the walls of the cutting chamber, is moved from above into the cutting chamber. The further pivoting of the lever causes the partly cut material to be pushed out of the cutting chamber through the second cutter at the bottom of the cutting chamber.

The disadvantage of this device is the complexity of its design. Likewise the cutting chamber is not easily accessible for cleaning. To chop the material it is necessary to perform two working strokes in opposite directions. First the lever must by pivoted in one direction in order to push the material through the first cutter and then the lever must be pivoted in the opposite direction in order to push the material through the second cutter.

DISCLOSURE OF INVENTION

The object of the present invention is to provide a device for cutting material, which has simple design, which is easily cleanable and where the chopping of the material is performed by one working stroke of the operating lever of the device.

The present invention provides a device for cutting material, mainly foods, vegetables or fruits, into cubes.

The device comprises housing and in the housing a rectangular cutting chamber with open top. Inside the cutting chamber there is placed a movable first cutter with cutting edges and at the bottom of the cutting chamber a stationary second cutter with cutting edges.

At one end of the cutting chamber there is placed a material ejector for removing material between the cutting edges of the first cutter.

Further the device comprises a lever attached to the housing and being pivotable around the pivoting axle, where in relation to the pivoting axle on one side of the lever a first cutter is attached in an articulated manner to the lever. When the lever is pivoted around the pivoting axle, the first cutter is moved linearly and parallel to the bottom of the cutting chamber from one end of the cutting chamber towards the first material ejector at the other end of the cutting chamber.

As a result of the movement of the first cutter the material to be cut in the cutting chamber is sliced into slices with the cutting edges of the first cutter in the cutting planes parallel to the bottom of the cutting chamber.

The device is characterized in that further pivotal movement of the lever in the same direction causes the first cutter to move into the first material ejector for ejecting material between the cutting edges of the first cutter and lever causes the second ejector attached to the other side of the lever in relation to the pivoting axle to enter into the cutting chamber.

By further pivotal movement of the lever the second ejector is made to move through the cutting chamber between the cutting edges of the second cutter for ejecting material through the cutting edges of the second cutter.

As a result of this operation, the chopped material is pushed out of the device, for example into the collecting container.

The movable first cutter comprises substantially parallel and uniformly spaced cutting edges with parallel cutting planes.

The second stationary cutter comprises two sets of parallel cutting edges, where the cutting planes of two sets of cutting edges being positioned at right-angles to each other.

Preferably the cutters are attached detachably to the device.

BRIEF DESCRIPTION OF DRAWINGS

The present invention is now described in greater detail with references to the accompanying drawings, in which.

BEST MODE FOR CARRYING OUT THE INVENTION

Figure 1:
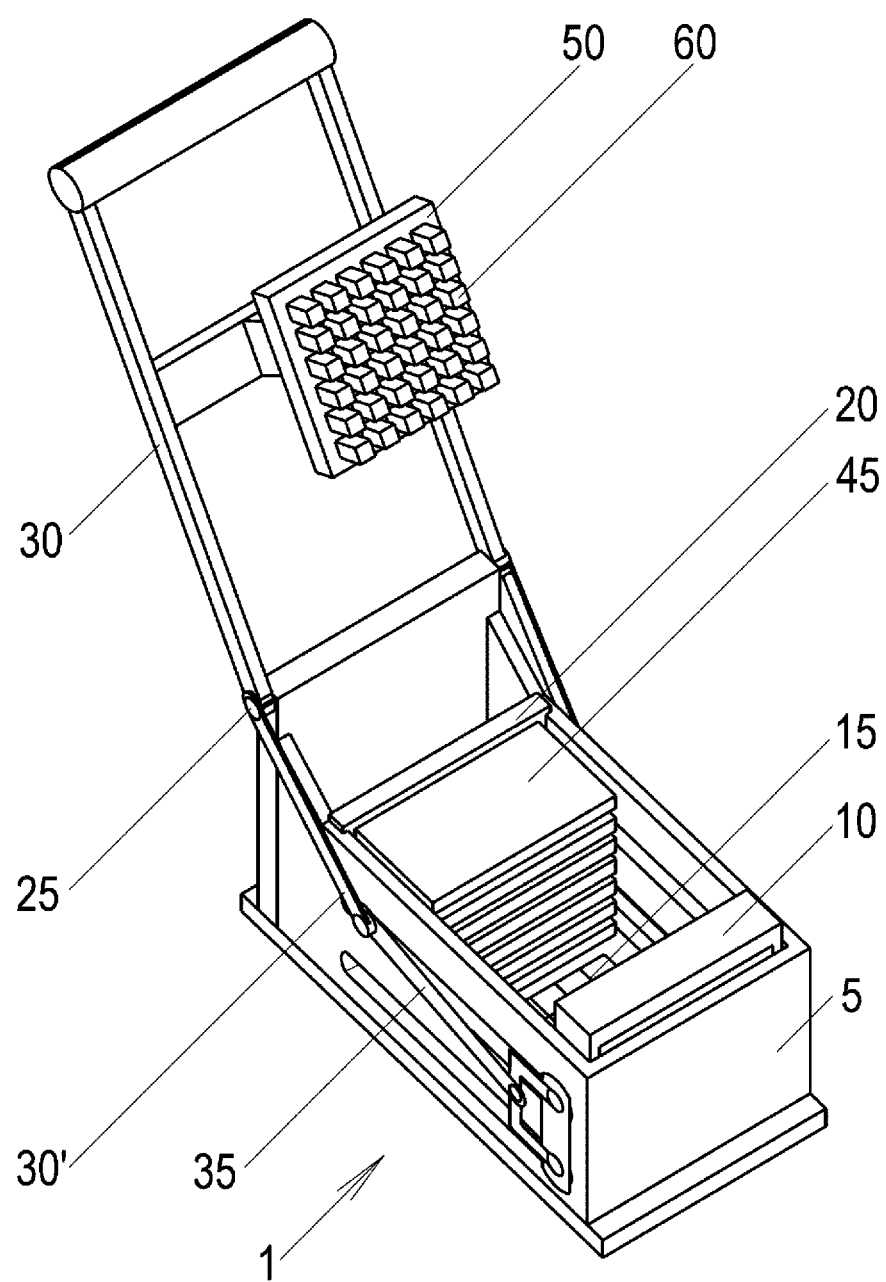
FIG. 1 represents a conceptual axonometric top view of the device according to the invention.

Device 1 in FIG. 1 comprises a housing 5 having a rectangular cutting chamber with open top. Inside the cutting chamber there is placed a movable first cutter 10. The bottom of the cutting chamber includes a stationary second cutter 15.

Figure 4:
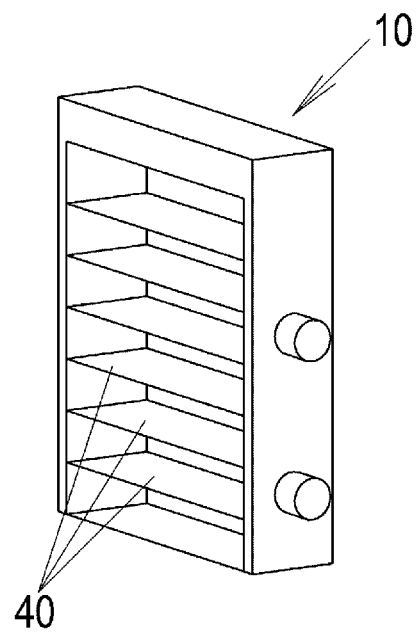
FIG. 4 represents a conceptual axonometric view of the first cutter with parallel cutting edges.

At one end of the cutting chamber (FIGS. 1 and 4) there is a material ejector 20 for pushing out the material from between the cutting edges of the first cutter 10.

A lever 30 is attached pivotally around the pivoting axle 25 to the housing 5, where in relation to the pivoting axle 25 on one side of lever 30' a first cutter 10 is attached in an articulated manner to the lever. In FIG. 1 the reference numbers 30 and 30' indicate the corresponding sides of the lever on either side of the pivoting axle 25. These portions of the level are attached rigidly together.

Figure 2:
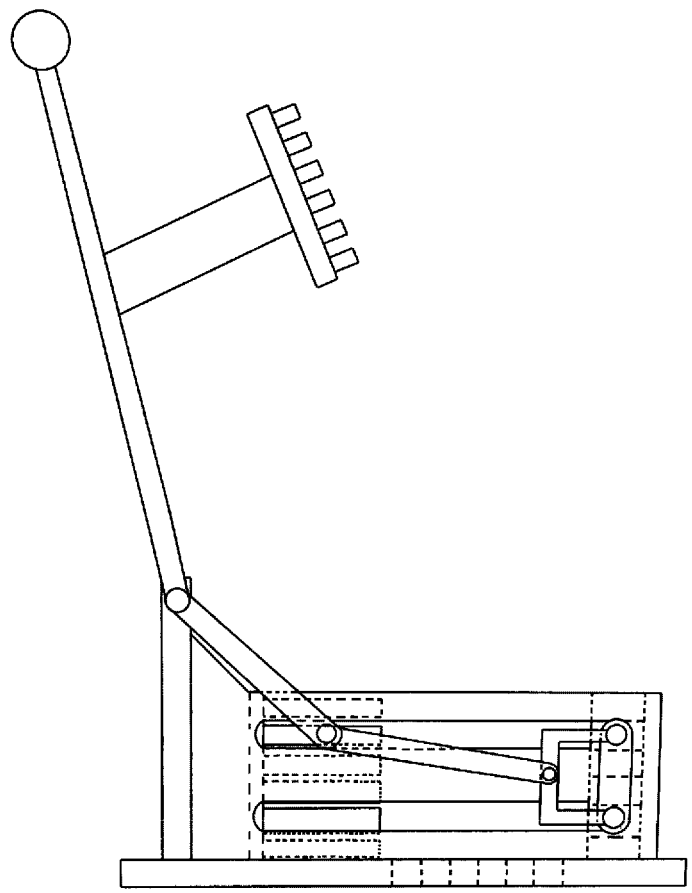
FIG. 2 represents a conceptual side view of the device according to the invention in a position before cutting the material.
Figure 3:
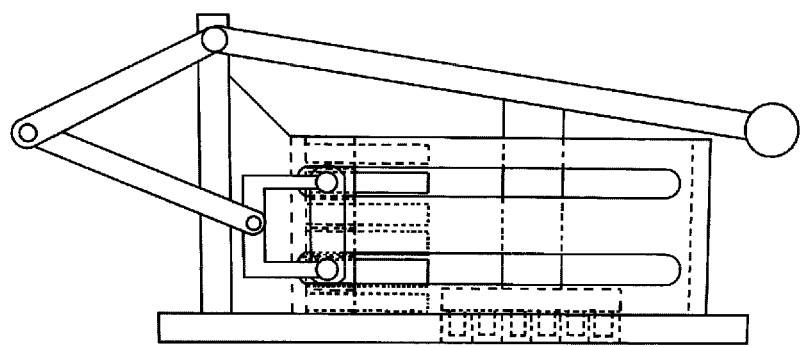
FIG. 3 represents a conceptual side view of the device according to the invention in a position after cutting the material.

The material (not shown) to be cut is placed in the position of the device 1 in FIGS. 1 and 2 into the housing 5 in front of the first cutter 10, that is into the housing onto the second cutter 15 at the bottom of the cutting chamber and between first cutter 10 and first ejector 20.

When the lever 30 is pivoted from the upright position in FIGS. 1 and 2 to the right, the first cutter 10 is moved parallel to the bottom of the cutting chamber from the one end of the cutting chamber towards the first material ejector 20 for ejecting material from between the cutting edges 40.

The first cutter 40 comprises parallel cutting edges 40, which are used to cut the material placed inside the cutting chamber into slices in cutting planes parallel to the bottom of the cutting chamber. Preferably the cutting edges 40 of the first cutter 10 are uniformly spaced.

As the pivoting of the lever 30, 30' in the same direction is continued, the first cutter 10 moves into the ejector 20 for ejecting material from between the cutting edges 40 of the first cutter 10, that is the cutting edges 40 of the first cutter 10 are placed interleaved with the protrusions 45 of the first ejector 20.

Figure 5:
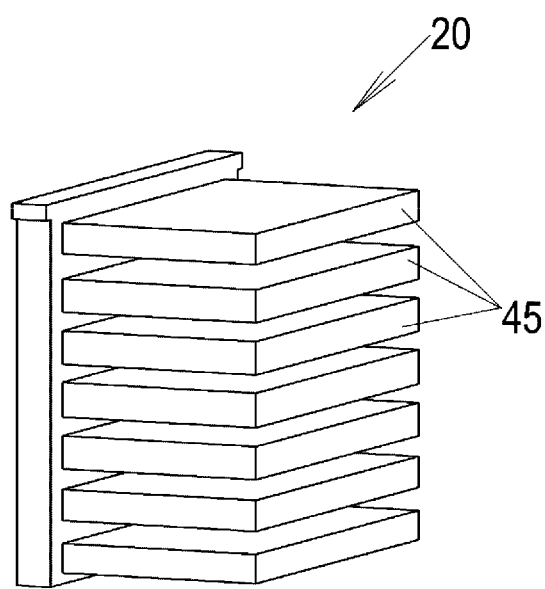
FIG. 5 represents a conceptual view of the first ejector for pushing material out from between the cutting edges of the first cutter.
Figure 6:
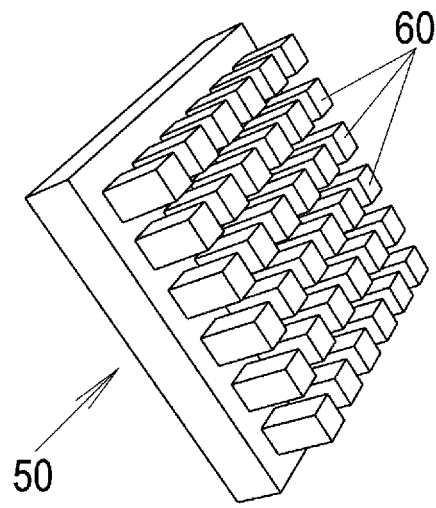
FIG. 6 represents a conceptual perspective view of the second ejector.

The first ejector 20 comprises rectangular protrusions 45 having thickness less than the spacing between the cutting edges 40 of the first cutter 10; see FIG. 5.

At the same time a second ejector 50 attached to the lever 30 at the other side of the lever 30 in relation to the pivoting axle 25 moves into the cutting chamber.

As the pivoting of the lever 30 is continued, the second ejector 50 is moved with its protrusions 60 between cutting edges 55, 55' of the second cutter 15, pushing the material to be cut in the cutting chamber through the cutting edges 55, 55' and out of the cutting chamber. The cut material is collected for example into a collecting container under the device.

The second cutter 15 at the bottom of the cutting chamber comprises two sets of cutting edges 55, 55. The cutting edges 55 of the first set are parallel to each other and uniformly spaced, whereby the spacing between the cutting edges preferably corresponds to the spacing between the cutting edges 40 of the first cutter.

The cutting edges 55' of the second set of the second cutter 15 are also parallel with each other and uniformly spaced, whereby the spacing between the cutting edges corresponds also to the spacing between the cutting edges 40 of the first cutter.

Figure 7:
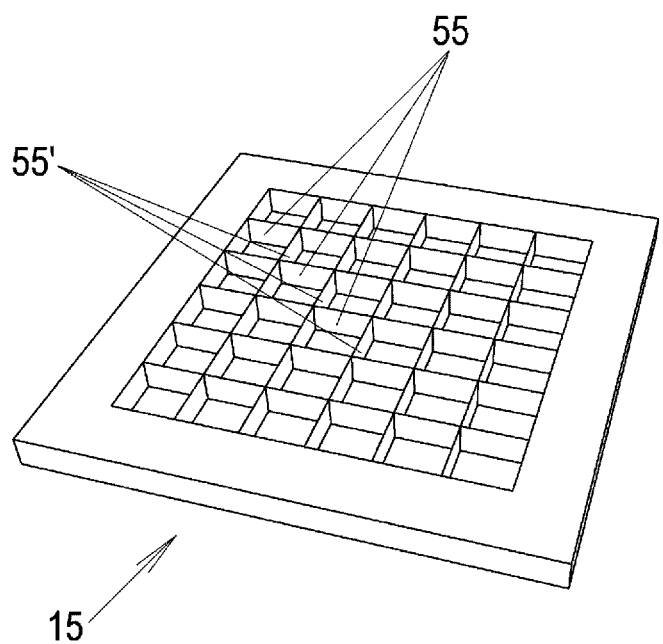
FIG. 7 represents a conceptual perspective view of the second cutter with crossing cutting edges.

The directions of the cutting edges 55 of the first set and the directions of the cutting edges 55' of the second set of the second cutter 15 are positioned at right-angles to each other. These edges form a so called cutting grid; see FIG. 7.

As a result of cutting of the material more or less cubic pieces are obtained.

Preferably the cutters 10 and 15 are attached detachably to the housing 5 of the device 1. This enables easy cleaning of the cutters. This makes it also possible to use the cutters with different spacing of the cutting edges in order to cut cubical pieces of a different size. In that case the ejectors must be also replaced, whereby the ejectors are also attached detachably to the device.

Also at the bottom of the cutting chamber a second cutter having different configuration of the cutting edges may be used, for example for cutting slices or strips instead of cubic pieces—at the bottom of the cutting chamber of the device for cutting material either only a cutter with parallel cutting edges or only the second cutter is used, The present invention is not limited to the exemplary embodiments described above, but in the scope of the accompanying claims many other embodiments are possible.

LIST OF REFERENCE NUMBERS

1—device
5—housing
10—first cutter
15—second cutter
20—first material ejector
25—pivoting axle of the lever
30, 30'—lever
35—linkage
40—cutting edges of the first cutter
45—protrusions of the first ejector
50—second ejector
55, 55'—cutting edges of the second cutter
60—protrusions of the second ejector

The invention claimed is:

1. A device for cutting material, mainly foods, vegetables or fruits, said device comprising:
a housing, said housing comprising a rectangular cutting chamber with an open top, in the cutting chamber there is a movable first cutter with a plurality of first cutting edges and at a bottom of the cutting chamber there is a stationary second cutter with a plurality of second cutting edges, and at one end of the cutting chamber there is a first material ejector for ejecting a material between the plurality of first cutting edges of the first cutter; and
a lever attached pivotally around a pivoting axle to the housing, wherein said first cutter is attached in an articulated manner to the lever such that when the lever is pivoted around the pivoting axle, the first cutter is caused to move linearly and parallel to the bottom of the cutting chamber from one end of the cutting chamber towards the first material ejector, wherein further pivotal movement of the lever causes the first cutter to move into the first material ejector for ejecting material between the plurality of first cutting edges of the first cutter, and wherein by further pivotal movement of the lever a second ejector attached to the lever is made to move through the cutting chamber between the plurality of second cutting edges of the second cutter for pushing the material through the plurality of second cutting edges of the second cutter.

2. The device according to claim 1, wherein the plurality of first cutting edges are substantially parallel and uniformly spaced.

3. The device according to claim 1, wherein the plurality of second cutting edges includes a first cutting plane with a first subset of parallel cutting edges and a second cutting plane with a second subset of parallel cutting edges positioned at a right-angle relative to the first cutting plane.

4. The device according to claim 1, wherein the plurality of first and second cutters are attached detachably to the housing of the device.

* * * * *